United States Patent [19]

Cummins, Jr. et al.

[11] Patent Number: 4,793,343
[45] Date of Patent: Dec. 27, 1988

[54] RESPIRATORY HEATED FACE MASK

[76] Inventors: James M. Cummins, Jr., 3334 Parker; George Morrison, Jr., 20637 Donaldson, both of Dearborn, Mich. 48124; Robert E. Pierfelice, 15218 Meyer, Allen Park, Mich. 48101

[21] Appl. No.: 87,398

[22] Filed: Aug. 20, 1987

[51] Int. Cl.$^4$ ............................................. A62B 7/00
[52] U.S. Cl. ........................ 128/204.17; 128/203.27; 219/364; 219/497; 219/501; 219/506
[58] Field of Search ............... 128/204.17, 203.26, 128/203.27, 206.17; 219/209, 210, 211, 364, 497, 501, 506, 527

[56] References Cited

U.S. PATENT DOCUMENTS

| | | | |
|---|---|---|---|
| 3,783,240 | 1/1974 | Drummond, Jr. | 219/527 |
| 3,903,395 | 9/1975 | Hamstra | 219/497 |
| 4,216,371 | 8/1980 | Marotel | 219/210 |
| 4,245,631 | 1/1981 | Wilkinson et al. | 128/204.17 |
| 4,279,255 | 7/1981 | Hoffman | 219/211 |
| 4,305,388 | 12/1981 | Brisson | 128/203.27 |
| 4,322,594 | 3/1982 | Brisson | 219/497 |
| 4,328,407 | 5/1982 | Chaggaris | 219/364 |
| 4,393,300 | 7/1983 | Proctor | 219/501 |
| 4,564,748 | 1/1986 | Gupton | 128/203.27 |
| 4,573,464 | 3/1986 | Yo | 128/206.17 |
| 4,601,287 | 7/1986 | Royce, Jr. | 128/204.17 |
| 4,620,537 | 11/1986 | Brown | 128/204.17 |
| 4,621,633 | 11/1986 | Bowles et al. | 128/204.17 |
| 4,682,010 | 7/1987 | Drapeau et al. | 128/204.17 |

FOREIGN PATENT DOCUMENTS 620266 7/1978 U.S.S.R. ........................ 128/205.25

Primary Examiner—Kyle L. Howell
Assistant Examiner—Timothy G. Philips
Attorney, Agent, or Firm—Barnes, Kisselle, Raisch, Choate, Whittemore & Hulbert

[57] ABSTRACT

A face mask for use in cold weather to supply warm air for inhalation by normal breathing to persons having respiratory and heart ailments to avoid the discomfort, pain and limited mobility caused by breathing cold air and to healthy people engaged in strenuous cold weather activities. The face mask has inlet and outlet check valves and a cold air intake chamber with an electric heater element therein which heats the cold air to supply warm air for inhalation. The heater element is preferably powered by a portable battery pack and controlled by electronic circuitry to maintain the heated air in a predetermined temperature range.

16 Claims, 2 Drawing Sheets

RESPIRATORY HEATED FACE MASK

FIELD OF THE INVENTION

This invention relates to a breathing mask and method for use in cold weather to supply warm air for inhalation to persons having respiratory and heart ailments and the like.

BACKGROUND OF THE INVENTION

Many breathing masks have been developed for protecting humans from exposure to a variety of particulate and gaseous matter. However, prior masks have been unsuccessful in supplying sufficiently heated air to persons having respiratory and heart ailments to enable them to move about and work normally outside in cold weather without experiencing discomfort and pain. Typically, this discomfort and pain is experienced by persons having respiratory conditions such as asthma, bronchitis, chronic bronchitis, emphysema or coronary conditions such as angina pectoris, post myocardial infarction, congestive heart failure, coronary heart disease, post coronary bypass and the like.

Usually such persons experience sufficient pain and discomfort that they must cease exerting themselves and get into a warm environment and rest. Hence, their activity in cold weather must be severely curtailed and in some instances substantially eliminated.

SUMMARY OF THE INVENTION

A face mask apparatus which obviates the pain and discomfort experienced by persons with many respiratory and heart ailments when breathing cold air by supplying warm air for inhalation. Cold air is heated and intermittently supplied in response to the normal breathing process through a face mask worn over the nose and mouth of a person. Cold air is heated for inhalation by an electric heater element carried by the mask and powered by an electric current. Preferably, the flow of air through the mask is controlled by inlet and outlet check valves responsive to the normal breathing process.

Preferably, the temperature of the heater element is controlled by suitable electronic circuitry to produce warm air for inhalation preferably having a temperature in the range of about 50° F. to 80° F. Preferably, the heater element is powered by a portable battery pack carried by the person. However, if desired, when the face mask is worn in a motor vehicle, the heater element can be powered by the electrical system of the motor vehicle to which it is preferably connected by being plugged into a cigarette lighter receptacle.

Objects, features and advantages of this invention are to provide an apparatus which greatly reduces and, in most instances, eliminates the discomfort and pain experienced by persons with many respiratory and heart ailments when exposed to cold weather, prevents hypothermia, is highly reliable, dependable, of relatively simple design and operation, and of economical manufacture, assembly and use.

BRIEF DESCRIPTION OF THE DRAWINGS

These and other objects, features and advantages of this invention will be apparent from the following detailed description, appended claims and accompanying drawings in which:

DETAILED DESCRIPTION

Figure 1:
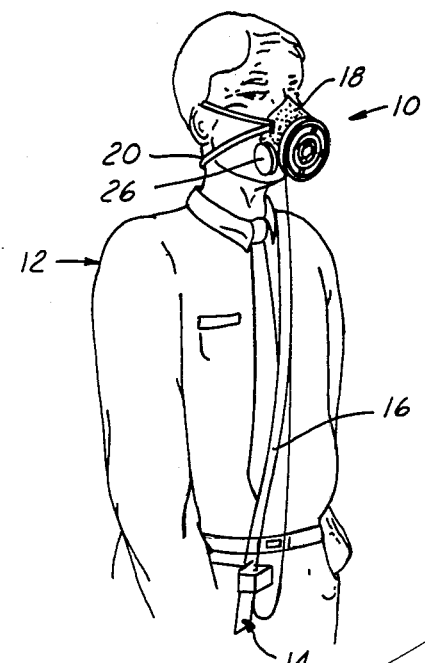
FIG. 1 is a fragmentary perspective view of a heated face mask apparatus embodying this invention being worn by a person.
Figure 2:
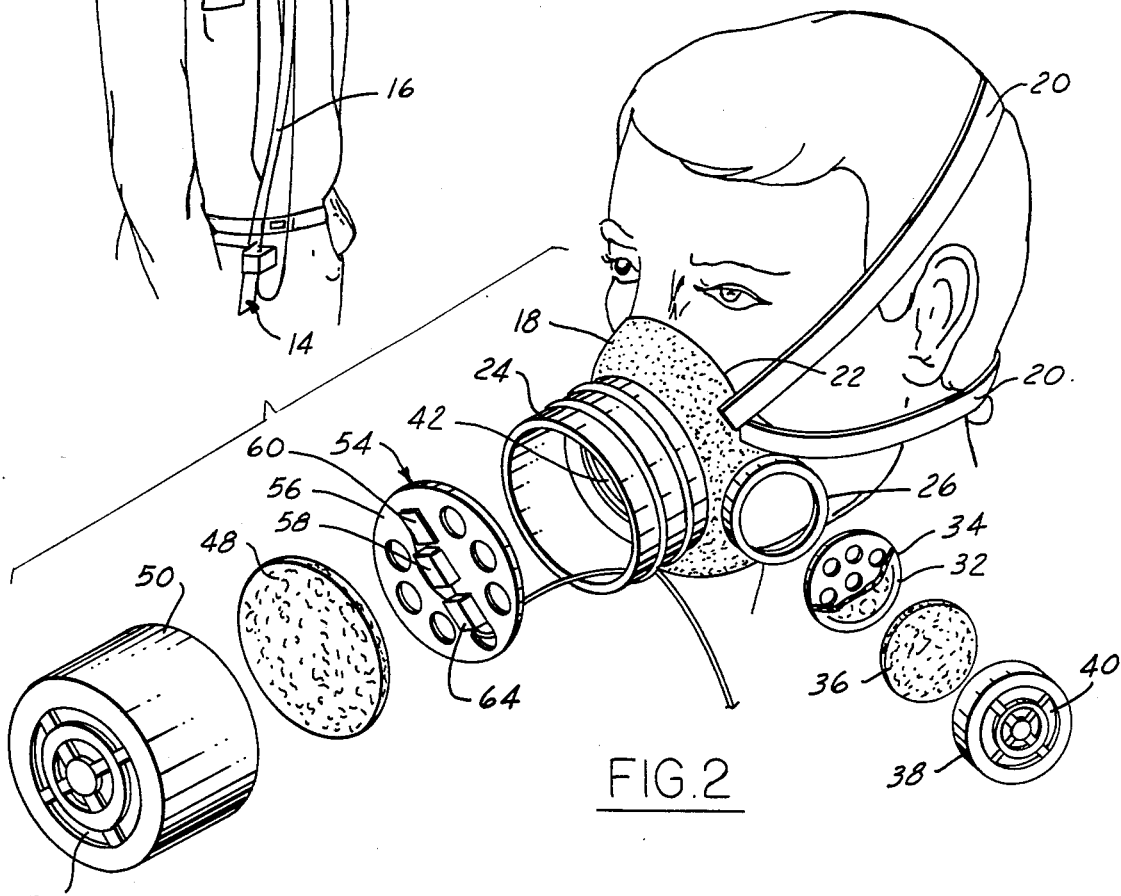
FIG. 2 is an exploded perspective view of the heated face mask of FIG. 1 illustrating some of its component parts.
Figure 3:
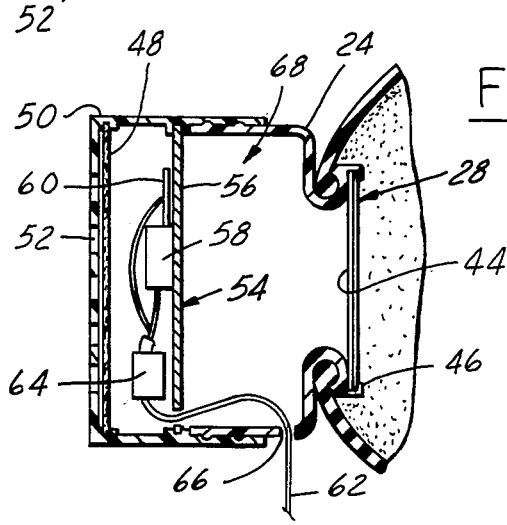
FIG. 3 is a fragmentary sectional view of an inlet, heater element and inlet valve assembly of the face mask of FIG. 1.

Referring in more detail to the drawings, FIG. 1 illustrates a face mask 10 embodying this invention being worn by a person 12 and powered by a battery and control pack 14 with a shoulder strap 16 received over the shoulder of the person. As shown in FIGS. 1 and 2, the face mask has a body housing 18 which in use encircles, overlies and encloses the nose and mouth of the person wearing the mask and is positioned and retained on the face by adjustable and preferably resilient straps 20 encircling the head. Preferably, the housing 18 is of a flexible material such as rubber and its outer periphery 22 will readily conform to the contour of the face and bear gently on the skin to provide a substantial gas-tight seal between the housing and the face of the wearer.

Figure 4:
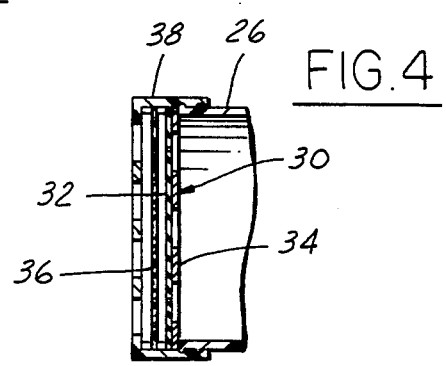
FIG. 4 is a fragmentary sectional view of an outlet and outlet valve assembly of the face mask of FIG. 1.

The face mask has an air inlet 24 and air outlets 26 carried by the housing 18 in which inlet and outlet check valve assemblies 28 and 30 are mounted. As shown in FIGS. 2 and 4, each outlet check valve assembly has a flexible diaphragm 32 providing a flap valve secured to a perforated carrier disc 34. The valve assembly and a filter disc 36 are mounted in assembled relation on the outlet 26 by a threaded cap 38 which is removably screwed thereon and has outlet air passages 40 therethrough.

The inlet check valve has a flexible diaphragm 42 providing a flap valve secured to a perforated carrier disc 44 which is removably received in a groove 46 adjacent the inner end of the inlet 24. A filter disc 48 is received in a threaded cap 50 removably screwed on the inlet 24 and having inlet air passages 52 therethrough. A suitable face mask, as thus far described, is commercially available from American Optical of Southbridge, Mass. 01550, as Model No. A/O R2090N.

In accordance with this invention, a heater assembly 54 is mounted in the inlet 24 to heat cold air to an elevated temperature to provide warm air for inhalation by the user of the mask. The heater assembly has a radiator and heat sink which is preferably a perforated disc 56 of a thermally conductive metal, such as aluminum. The disc is heated by an electric resistance element, such as a power transistor 58 in heat transfer relationship with the disc. Preferably, the power transistor is fixed to the disc by a mechanical fastener such as a bolt or rivet or an adhesive such as an epoxy. Preferably, to sense the temperature of the radiator disc for controlling the temperature of the air heated by it, a thermistor 60 is also mounted on the disc in heat transfer relationship with it by an adhesive such as an epoxy. An electric current is supplied to the power transistor through a suitable electric cable 62 which is anchored to the disc by a restrainer block 64 and passes through a hole 66 in the inlet.

A chamber 68 in which the cold air is heated is defined by the inlet 24, cap 50 and inlet check valve assembly 28. The air is primarily heated as it passes through the heater assembly 54 during inhalation. It has been found to be very satisfactory for the chamber 68 to have a volume of about 3 to 10 cubic inches.

CONTROL CIRCUIT

Figure 5:
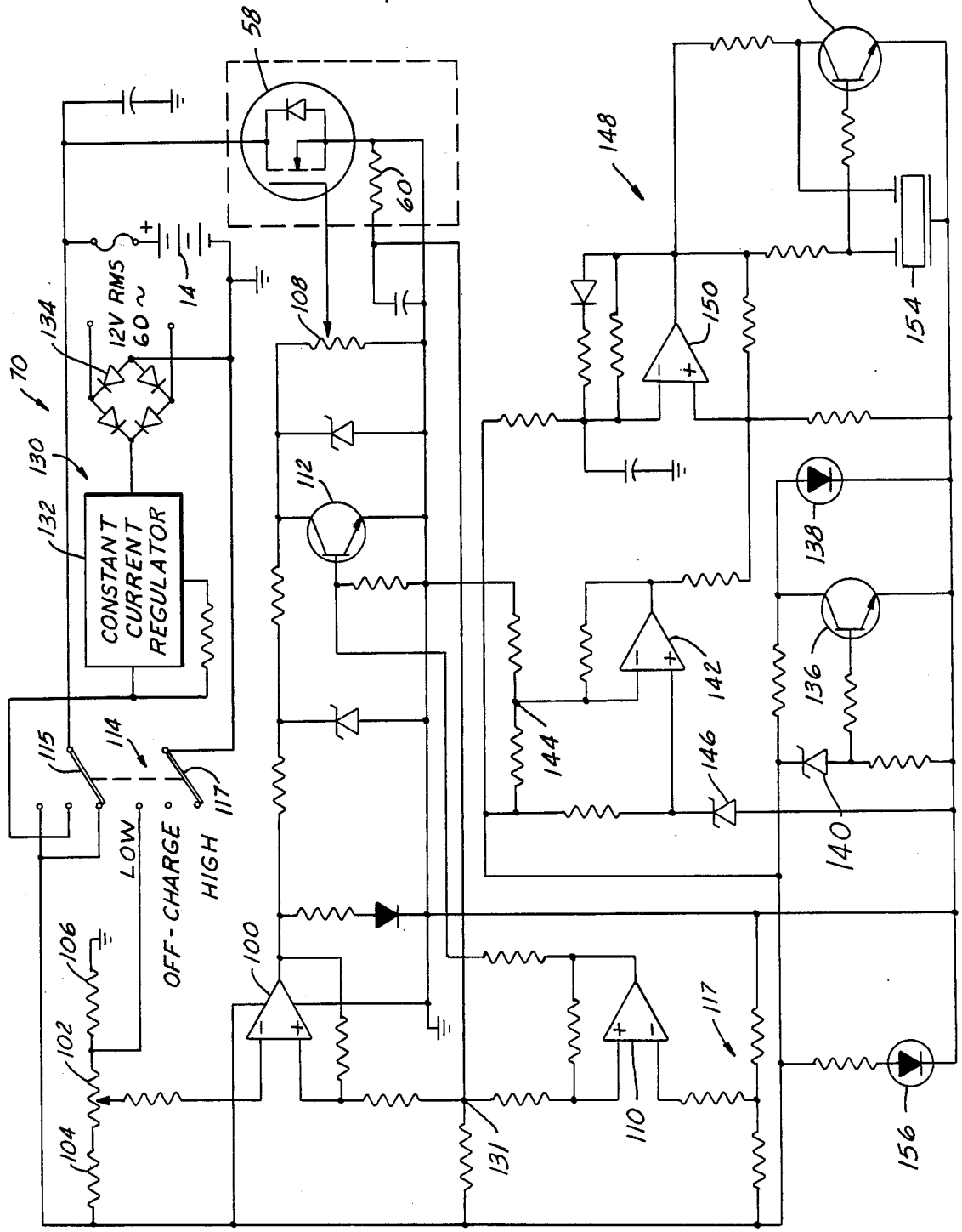
FIG. 5 is an electrical schematic diagram of a suitable electronic control for the heater element of the face mask of FIG. 1.

In accordance with another feature of this invention, the temperature to which the air to be inhaled is heated, is adjusted within predetermined limits and controlled by a control circuit 70 shown schematically in FIG. 5. The control circuit has a first comparator 100 having a non-inverting input connected to the thermistor 60 and an inverting input connected to a available resistor 102. Resistor 102 is connected in series with resistors 104, 106 to form a voltage divider across the battery power 14. The output of comparator 100 drives the gate of the MOSFET power transistor 58 through a second variable resistor 108. A second comparator 110 has an inverting input connected to a voltage divider 117 across battery power and a non-inverting input connected to the thermistor 60. The output of comparator 110 is connected to the base of a transistor 112 which has its emitter and collector connected between the output of comparator 100 and ground (through current limiting resistors).

A double-pole, triple throw switch 114 has a first contact 115 connected to battery 14 for supplying battery power to the temperature control electronics. The second pole 117 of switch 114 has its common contact connected to ground and one of its normally-open contacts connected to the junction of resistors 102 and 106. At the center position of switch 114, contact 115 connects battery 14 to a charging circuit 130 which includes a constant current regulator 132 coupled through a diode bridge 134 to a suitable source of A.C. power (not shown). An NPN transistor 136 has collector and emitter contacts connected across a low-battery LED 138 coupled to battery power, and a base connected through a zener diode 140 to battery power.

A compartor 142 has its inverting input connected to battery power through the voltage divider 144, and its non-inverting input connected across the zener diode 146. The output of compartor 142 drives a voltage-to-frequency converter 148 which includes a compartor 150 and a transistor 152. Transistor 152 drives a piezo-electric buzzer 154.

CONTROL CIRCUIT OPERATION

In operation, and with the switch 114 in the "high" position shown, comparator 100 energizes MOSFET 58 when the temperature of the heat radiator disc 56 (FIG. 2) detected by thermistor 60 is below the reference level set by resistor 102 in combination with resistors 104, 106. That is, as the temperature of the heat radiator 56 drops and the resistance of the thermistor 60 correspondingly increases, the voltage at the non-inverting input of comparator 100 eventually exceeds the voltage at the inverting input, so that the comparator output drives MOSFET 58 through resistor 108. Resistor 102 thus effectively sets the temperature at which comparator 100 energizes MOSFET 58, and resistor 108 sets the MOSFET drive voltage when comparator 100 is turned on.

As MOSFET 58 heats radiator disc 56 and the resistance of thermistor 60 drops accordingly, the voltage at the non-inverting input of comparator 100 eventually decreases below that at the inverting input, and comparator 100 terminates the drive voltage to the MOSFET 58. Hysteresis at comparator 100 prevents oscillation of the comparator and drive circuit about the set point of resistor 102. When switch 114 is placed in the "low" position, resistor 106 is effectively short circuited, thus changing the effective set point of resistor 102 and comparator 100. Thus, switch 114 cooperates with the voltage divider consisting of resistors 102-106 to provide differing "high" and "low" temperature sensitivities.

Comparator 110 clamps the output of comparator 100 and inhibits operation of the MOSFET 58 in the event that thermistor 60 fails in the open-circuit mode. That is, if thermistor 60 fails in the open-circuit mode, the voltage applied to the non-inverting input of comparator 110 will exceed the reference level at the inverting input set by resistor voltage divider 117, and the output of comparator 110 will turn on transistor 112. In this event, the collector of transistor 112 effectively clamps the output of comparator 100 through its emitter to ground, so that energizing voltage cannot be applied to MOSFET 58 through resistor 108. In the event that thermistor 60 fails in the short-circuit mode so as to effectively ground junction 131, the voltage at the non-inverting input of comparator 100 will not exceed that at the inverting input at either the "high" or "low" position of switch 114, so that comparator 100 will not energize the MOSFET 58.

Application of battery power energizes the power-on LED 156. As long as the battery voltage remains above the level determined by zener diode 140, transistor 136 shunts current from LED 138. However, when battery voltage declines, transistor 136 turns off and "low battery" LED 138 is energized. Comparator 142 drives V/F converter 148 at a level which varies as a function of comparison between battery voltage divider 144 and the reference level set by zener diode 146. As battery voltage declines below the reference level of zener diode 146, drive voltage to converter 148 increases and the frequency of energization of buzzer 154 increases accordingly. Thus, the wearer is continuously advised by buzzer 154 not only that battery charge is decreasing, but also the level of declining charge. As long as the voltage at divider 144 remains above the level set by zener diode 146, compartor 142 and buzzer 154 remain off.

FACE MASK OPERATION AND USE

Typically, the face mask is used by a person having a respiratory or heart condition in which they will experience discomfort and pain if they breathe cold air, such as when being outside in cold weather, and particularly if they are active or exerting themselves while in the cold air. It can also be used by healthy persons engaging in strenuous activity in cold weather such as construction work and recreational activities. In use, the face mask 10 is placed over the nose and mouth of the person (as shown in FIGS. 1 and 2), and secured to and retained on the persons head by adjustable and preferably resilient straps.

In use of the mask, the person breathes in the normal manner. When the person inhales, inlet valve 28 opens and cold air is drawn from the exterior atmosphere through the inlet 24 and the chamber 68 where it is heated by heater assembly 54. The heated air is then drawn through the valve 28, housing 16 and into the nose and/or mouth of the person. While the person is inhaling, the outlet check valves 30 remain closed. When the person exhales, the air emitted from the person's nose and/or mouth is discharged into the housing 18 and through the outlet valves 30 to the atmosphere exteriorly of the mask. While the person is exhaling the inlet valve 28 remains closed.

The radiator disc 56 of the heater assembly is heated by the power transistor 58 to which an electric current is supplied through the control circuit 70 and connecting wires 62. Preferably, current is supplied to the control circuit by the portable battery pack 14 carried by the user. However, if desired, current can be supplied from the electric system of a motor vehicle preferably through an appropriate connector (not shown) plugged into a receptacle for a cigarette lighter, or from any other suitable power source. The temperature to which the radiator disc 56 is heated, and hence the temperature of the air inhaled by the user, is controlled and varied within predetermined limits by the control circuit 70. This is accomplished by the thermistor 60 which senses the temperature of the disc 58 and its associated circuitry which intermittently turns the power transistor 58 on and off. The control circuit 70 has a high heat range and a low heat range provided by the switch 114 and associated circuitry. An indication that the control circuit has been turned on by the switch is provided by a light emitting diode 156 and associated circuitry. An indication that the battery of the power supply is running low and should be recharged or replaced is provided by light-emitting diode 138 and buzzer 154. Heating of the air to an excess temperature due to a malfunction of the temperature sensing thermistor 60 is prevented by associated fault detecting circuitry which automatically turns off the current to the power transistor 58.

We claim:

1. A respiratory apparatus which comprises: a face housing constructed and arranged for overlying and encircling the nose and mouth of a person when received on their face, an intake housing having an air intake chamber and carried by said face housing, an inlet check valve carried by said face housing and constructed and arranged to permit air to pass from said chamber through said valve and into said face housing when the wearer of the mask inhales and to prevent air from passing from said face housing into said chamber when the wearer exhales, an exhaust check valve carried by said face housing and constructed and arranged to permit air to pass from said face housing through said exhaust valve to the exterior of said face housing when the wearer of the mask exhales and to prevent air from passing through said exhaust valve and into said face housing when the wearer of the mask inhales, and a heater assembly having an electric heating element means, a radiator means disposed in said chamber and in heat transfer relationship with said heating element means and constructed and arranged to heat air in said chamber when an electric current is supplied to said heating element means, whereby cold air drawn into said chamber is heated by said heater assembly to an elevated temperature to supply warm air to be inhaled by the wearer of the mask, a temperature sensor means for sensing the temperature of said radiator means with respect to an adjustable reference level and producing an associated electronic temperature sensor signal, an electronic control circuitry means constructed and arranged to receive said temperature sensor signal and having a current supply means connected to a portable power supply means for selectively and controllably supplying current to said electric heating element means in response to said temperature sensor signal, a means for sensing failure of said temperature sensor means and a means for inhibiting operation of said heating element means in the event of failure of said temperature sensor means.

2. The apparatus of claim 1 which also comprises a cap removably receivable on said intake housing and having air inlets therethrough, and said heater assembly being disposed in said intake housing between said cap and said inlet check valve.

3. The apparatus of claim 2 which also comprises an air filter disposed between said cap and said heater assembly.

4. The apparatus of claim 2 wherein said intake chamber has a volume of at least about 3 cubic inches.

5. The apparatus of claim 1 wherein said portable power supply means comprises, a portable power pack having a battery for supplying an electric current to said heating element means, and means for carrying said power pack by the wearer of the face mask.

6. The apparatus of claim 5 wherein carrying means comprises a shoulder strap for carrying said power pack by the wearer of the face mask.

7. The apparatus of claim 1 wherein said electric heating element means comprises a power transistor in heat transfer relationship with said radiator means.

8. The apparatus of claim 7 wherein said radiator means is of metal.

9. The apparatus of claim 7 wherein said temperature sensor means comprises a thermistor in heat transfer relationship with said radiator means and wherein said electronic control circuitry means is electrically connected to said thermistor and said power transistor to sense the temperature of said radiator means and supply current to said power transistor to control within predetermined limits the temperature to which said radiator means is heated by said power transistor.

10. The apparatus of claim 9 wherein said portable power supply means comprises a power pack having a battery connectable to said control circuitry means and through said control circuitry means to said power transistor.

11. The apparatus of claim 10 wherein said power pack also comprises a shoulder strap for carrying the power pack by the wearer of the face mask.

12. The apparatus of claim 7 wherein said electronic control circuitry means further comprises a means for supplying current to said heating element means when temperature sensed by said temperature sensor means is less than said reference temperature.

13. The apparatus of claim 12 wherein said current-supplying means further comprises means for selectively varying said reference temperature signal.

14. The apparatus of claim 13 wherein said current-supplying means comprises a comparator for supplying current to said heating element means when said temperature signal is less than said reference signal.

15. The apparatus of claim 14 wherein said electronic control circuitry means comprises a voltage divider, and wherein said reference-varying means comprises operator switch means coupled to said voltage divider for varying said reference signal as a function of conductive condition of said switch means.

16. The apparatus of claim 14 wherein said failure-sensing means comprises a second comparator having a first input for receiving said temperature signal and a second input for receiving a failure reference signal, and wherein said operation-inhibiting means comprises switch means operatively coupled to said heating element for interrupting supply of current thereto.

* * * * *